(12) United States Patent
Fine (10) Patent No.: US 7,254,432 B2
(45) Date of Patent: Aug. 7, 2007

(54) METHOD AND DEVICE FOR NON-INVASIVE MEASUREMENTS OF BLOOD PARAMETERS

(75) Inventor: Ilya Fine, Rehovot (IL)

(73) Assignee: Orsense Ltd., Rehovot (IL)

( * ) Notice: Subject to any disclaimer, the term of this patent is extended or adjusted under 35 U.S.C. 154(b) by 0 days.

(21) Appl. No.: 11/205,321

(22) Filed: Aug. 17, 2005

(65) Prior Publication Data
US 2007/0043281 A1    Feb. 22, 2007

(51) Int. Cl.
*A61B 5/00*    (2006.01)

(52) U.S. Cl. ...................................... 600/335; 600/322

(58) Field of Classification Search ................ 600/316, 600/317, 322, 323, 335
See application file for complete search history.

(56) References Cited

U.S. PATENT DOCUMENTS

| | | |
|---|---|---|
| 3,412,729 A | 11/1968 | Smith, Jr. |
| 4,463,462 A | 8/1984 | Rubens |
| 4,714,341 A | 12/1987 | Hamaguri et al. |
| 4,786,394 A | 11/1988 | Enzer et al. |
| 4,883,055 A | 11/1989 | Merrick |
| 4,927,264 A | 5/1990 | Shiga et al. |
| 4,975,581 A | 12/1990 | Robinson et al. |
| 5,054,487 A | 10/1991 | Clarke |
| 5,069,214 A | 12/1991 | Samaras et al. |
| 5,111,817 A | 5/1992 | Clark et al. |
| 5,277,181 A | 1/1994 | Mendelson et al. |
| 5,282,467 A | 2/1994 | Piantadosi et al. |
| 5,638,816 A | 6/1997 | Kiani-Azarbayjany et al. |
| 5,827,181 A | 10/1998 | Dias et al. |
| 5,931,779 A | 8/1999 | Arakaki et al. |
| 6,400,972 B1 | 6/2002 | Fine |
| 6,587,704 B1 * | 7/2003 | Fine et al. .................. 600/335 |

(Continued)

FOREIGN PATENT DOCUMENTS

EP    227119 A2    7/1987

(Continued)

OTHER PUBLICATIONS

Kye Jin Jeon et al "Noninvasive total hemoglobin measurement" Journal of Biomedical Optics (Jan. 2002) vol. 7, No. 1, pp. 45-50.

(Continued)

*Primary Examiner*—Eric Winakur
*Assistant Examiner*—Etsub Berhanu
(74) *Attorney, Agent, or Firm*—Browdy and Neimark, PLLC (57) ABSTRACT

A method and system for non-invasive measurements in a patient's body in which several measurement sessions are performed on a measurement location. Each measurement session includes applying an external electromagnetic field to the measurement location, detecting at least two responses of the measurement location, and generating data indicative of the detected response. These responses are characterized by at least two different values of a controllable parameter. The measurement sessions include at least two measurement sessions carried out at a normal blood flow in the measurement location and at least two measurement sessions carried out at a condition of artificial kinetics in the measurement location. The first and second measured data are processed to determine a first relation between the first time variations and a second relation between the second time variations for the different parameter. that can be used to determine the at least one blood related parameter.

11 Claims, 5 Drawing Sheets

U.S. PATENT DOCUMENTS

| 6,606,509 B2 | 8/2003 | Schmitt |
|---|---|---|
| 6,711,424 B1 | 3/2004 | Fine et al. |
| 6,804,002 B2 | 10/2004 | Fine et al. |

FOREIGN PATENT DOCUMENTS

| WO | 9817174 A1 | 4/1998 |
|---|---|---|
| WO | 0009004 A2 | 2/2000 |
| WO | 2004105596 A1 | 12/2004 |

OTHER PUBLICATIONS

Lindberg et al., "Partial Least-Square Method for Spectrofluorimetric Analysis of Mixtures of Humic Acid and Ligninsulfonte", Analytical Chemistry, 1983, vol. LV, pp. 643-647.

Wood et al., "Photoelectric Determination of Arterial Oxygen Saturation in Man", Journal of Laboratory and Clinical Medicine, Jun. 1949, vol. 34, No. 1, pp. 397-401.

* cited by examiner

METHOD AND DEVICE FOR NON-INVASIVE MEASUREMENTS OF BLOOD PARAMETERS

FIELD OF THE INVENTION

This invention is generally in the field of non-invasive measuring techniques and relates to a method for non-invasive measurements of blood parameters, such as the concentration of a substance in blood (e.g., hemoglobin, glucose, drugs or cholesterol), or other important blood parameters such as oxygen saturation.

BACKGROUND OF THE INVENTION

Various non-invasive techniques have been developed for determining blood-related parameters such as hemoglobin, hematocrit, oxygen saturation, etc. These techniques are disclosed for example in the following publications:

A pulse oxymetry based hemoglobin measurement technique is described in the article *"Noninvasive total hemoglobin measurement"*, by Kye Jin Jeon et al., Journal of Biomedical Optics 7(1), 45-50, January 2002. This technique consists of a wavelength selection and prediction algorithm for determining total hemoglobin concentration. A model has been developed, based on the difference in optical density induced by the pulsation of the heart beat, by taking an approximation of Twersky's theory on the assumption that the variation of blood vessel size is small during arterial pulsing. The device utilizes a five wavelength light emitting diode array as the light source. The selected wavelengths are two isobestic points and three in compensation for tissue scattering. Data are collected from 129 outpatients who are randomly grouped as calibration and prediction sets. The ratio of the variations of optical density between systole and diastole at two different wavelengths is used as a variable. Several such variables have been selected that show high reproducibility among all variables. Multiple linear regression analysis has been made in order to predict total hemoglobin concentration. The correlation coefficient is 0.804 and the standard deviation is 0.864 g/dL for the calibration set. The relative percent error and standard deviation of the prediction set are 8.5% and 1.142 g/dL, respectively. These investigations demonstrate the possibility of noninvasive hemoglobin measurement, particularly, using the wavelengths below 1000 nm.

U.S. Pat. No. 5,277,181 discloses noninvasive measurement of hematocrit and hemoglobin content by differential optical analysis. This technique utilizes differential optical absorption of two or more wavelengths of light during blood volume changes. The method is also useful for noninvasive measurements of other blood analytes, such as glucose, where variations in hematocrit or blood hemoglobin concentration cause errors in the measurement.

U.S. Pat. No. 4,927,264 discloses a non-invasive measuring method and apparatus of blood constituents. Here, in order to measure the oxygen saturation in venous blood, a venous blood stream is made time-variant by applying pressure with a peak value of the minimum blood pressure to a proximal portion from a measuring part. Light beams with different wavelengths are transmitted from the measuring part and detected by photodiodes. Photodetected signals are logarithm-converted and venous signal components are separated from logarithm-converted signals with a filter circuit. The oxygen saturation of venous blood is calculated on the basis of separated venous signal components.

U.S. Patent No. 5,827,181 describes a noninvasive blood chemistry measurement method and system that isolate measurement contributions due to a patient's blood to accurately measure blood chemistry. According to one embodiment, a noninvasive blood chemistry measurement method decreases the blood volume within a patient's body part relative to the normal blood volume in the body part and performs a baseline measurement. Blood volume is then increased and a second measurement is performed. Comparison of the second measurement to the baseline measurement isolates the measurement attributes of the patient's blood. In accordance with another embodiment, a noninvasive blood chemistry measurement system decreases blood volume by applying mechanical pressure to a body part. According to yet another embodiment, blood volume in the body part is decreased using a pressure cuff. In a further embodiment, a noninvasive probe accurately measures blood chemistry and uses a suction cup to increase blood volume at the blood chemistry measurement site.

U.S. Pat. No. 6,606,509 discloses a method and apparatus for improving the accuracy of noninvasive hematocrit measurements. According to this technique, the changes in the intensities of light of multiple wavelengths transmitted through or reflected light from the tissue location are recorded immediately before and after occluding the flow of venous blood from the tissue location with an occlusion device positioned near the tissue location. As the venous return stops and the incoming arterial blood expands the blood vessels, the light intensities measured within a particular band of near-infrared wavelengths decrease in proportion to the volume of hemoglobin in the tissue location; those intensities measured within a separate band of wavelengths in which water absorbs respond to the difference between the water fractions within the blood and the displaced tissue volume. A mathematical algorithm applied to the time-varying intensities yields a quantitative estimate of the absolute concentration of hemoglobin in the blood. To compensate for the effect of the unknown fraction of water in the extravascular tissue on the hematocrit measurement, the tissue water fraction is determined before the occlusion cycle begins by measuring the diffuse transmittance or reflectance spectra of the tissue at selected wavelengths.

A different approach is disclosed in various patents assigned to the assignee of the present application, such as for example U.S. Pat. No. 6,400,972; U.S. Pat. No. 6,587,704; U.S. Pat. No. 6,711,424; and U.S. Pat. No. 6,804,002. These techniques provide for measurement of various parameters of the patient's blood, based on the creation of a condition of artificial kinetics at a measurement location, and maintaining this condition during a certain time. Measurements are carried out during a time period including this certain time by applying an external electromagnetic field to the measurement location and detecting a response to the applied field. Measured data is in the form of time evolutions of the responses of the medium corresponding to the different parameters of the applied field. By analyzing the measured data, at least one blood parameter is extracted.

SUMMARY OF THE INVENTION

There is a need in the art to facilitate non-invasive measurements of various blood parameters, by providing a novel method and device capable of providing the improved accuracy of measurements.

The inventors have found a certain problem associated with the fact that the methodology of each of the known approaches is based on a different kind of blood related signal. More specifically, pulsatile measurements (e.g., the above-indicated article "*Noninvasive total hemoglobin measurement*", by Kye Jin Jeon et al., Journal of Biomedical Optics 7(1), 45-50, January 2002; U.S. Pat. No. 5,277,181) are based on the arterial blood natural volumetric changes. Under-systolic volume manipulation based measurements (e.g., the above-indicated patents U.S. Pat. No. 4,927,264; U.S. Pat. No. 5,827,181; U.S. Pat. No. 6,606,509) deal with venous blood. Over-systolic occlusion based measurements (disclosed in the aboveindicated patents U.S. Pat. No. 6,400,972; U.S. Pat. No. 6,587,704; U.S. Pat. No. 6,711,424; and U.S. Pat. No. 6,804,002) are based on the arterial blood artificial kinetics (changes in a medium response caused by the Red Blood Cells (RBCs) aggregation). The physical and physiological principals underlying the pulsatile signal, under-systolic volumetric signal and post occlusion signals are essentially different. The pulsatile and under-systolic volumetric signals originate mainly from the natural volume changes (although aggregation-related signal may interfere with this changes), whereas during the post occlusion period of time the volume is kept constant and aggregation process dominates.

The inventors have found that the accuracy of measurements could be improved by appropriately combining occlusion (no pulse due to blood flow cessation) and pulse modes of measurements. Occlusion mode is that of artificial kinetics condition, namely RBC aggregation effect drives the major changes of the medium response to an applied electromagnetic field. Pulse mode is a volumetric driven mode of operation, namely response signal changes are driven mainly by changes of quantity of the blood. By appropriately utilizing both of the occlusion and pulse modes, the accuracy of measurements can be improved. According to the invention, measurements are applied to the region of interest in a blood-perfused fleshy medium under occlusion and before and/or after the occlusion—to the same region at the steady state (non-occluded) thereof.

The measurements may include the so-called "pure optical" measurements, namely, illumination of a measurement location and detection of a light response thereof (transmission or reflection/scattering), and/or photo-acoustic spectroscopy (illumination of a measurement location and detection of acoustic response thereof), and/or impedance based measurements (total electrical resistance or a component of the impedance) according to which two electrodes are brought into direct contact with the human body and real and imaginary components of reflected and/or transmitted electromagnetic signals are spectrally examined as a function of frequency. The measurements are taken with at least two different values of a controllable parameter. The latter may include the parameter of the applied electromagnetic field; and/or in case of optical measurements of the concentration of an optically active (scattering) substance (such as glucose)—polarization states of detected light.

There is thus provided according to one broad aspect of the invention, a method for use in non-invasive measurements in a patient's body, the method comprising:

(a) performing several measurement sessions on a measurement location on the body, each measurement session comprising applying an external electromagnetic field to a measurement location and detecting at least two responses of the measurement location characterized by at least two different values of a controllable parameter, and generating data indicative of the detected response, wherein the measurement sessions include at least two measurement sessions carried out at a normal blood flow in the measurement location enabling generation of first measured data indicative of a first time variation of the response for each of said at least two parameter values, and at least two measurement sessions carried out at a condition of artificial kinetics in the measurement location enabling generation of second measured data indicative of a second time variation of the response for each of said at least two parameter values; and (b) processing the first and second measured data to determine a first relation between the first time variations for the different parameter values and a second relation between the second time variations for said different parameter values; and (c) utilizing the first and second relations to determine the at least one blood related parameter.

The condition of artificial kinetics may be created by applying over-systolic pressure to the vicinity of the measurement location, or to a location on the body upstream of the measurement location with respect to a normal blood flow direction in the body.

Preferably, the invention utilizes optical measurements: The measurement session may include illuminating the measurement location with at least two different wavelengths of light (constituting at least two different values of the applied field parameter) and detecting the light response of the body portion (e.g., light transmitted through the body portion under measurements). Alternatively, the measurement session may include illuminating the measurement location with at least one wavelength of light and detecting the light response of the body portion while at different polarization states of the detected light (constituting at least two different values of the controllable parameter).

Preferably, each of the first and second relations is determined as a parametric slope of the respective time functions of the responses. A pair of the first and second parametric slopes $PS_1$ and $PS_2$ obtained for the same pair of wavelengths $\lambda_1$-$\lambda_2$ (constituting pair of the applied field parameter values) are determined as:

$$PS_1 = \frac{\partial \mathrm{Ln}(I^1\lambda 1)/\partial(t)}{\partial \mathrm{Ln}(I^1\lambda 2)/\partial(t)}$$

and $$PS_2 = \frac{\partial \mathrm{Ln}(I^2\lambda 1)/\partial(t)}{\partial \mathrm{Ln}(I^2\lambda 2)/\partial(t)}$$

wherein $I^1$ and $I^2$ are the first and second light responses and t is time.

The desired blood parameter BP can be determined as $$BP = \sum_{i=1}^{N} A_i \cdot (PS_1)_i + \sum_{i=1}^{M} B_i \cdot (PS_2)_i,$$

wherein $A_i$ and $B_i$ are calibration coefficients; $(PS_1)_i$ and $(PS_2)_i$ are first and second parametric slopes obtained for the same pair of wavelengths; and i is a number of wavelength.

The measurement sessions carried out at the normal blood flow condition may be performed before or after the measurement sessions under the artificial kinetics condition.

The blood related parameter that can be determined by the technique of the invention includes concentration of substance (e.g., hemoglobin, hematocrit, glucose) in blood and/or oxygen saturation.

According to another broad aspect of the invention, there is provided a method for use in non-invasive measurements in a patient's body, the method comprising:

(a) performing several optical measurement sessions on a measurement location on the body, each measurement session comprising illuminating a measurement location and detecting light responses of the measurement location characterized by at least two different values of a controllable parameter, and generating data indicative of the detected light response, wherein the measurement sessions include at least two measurement sessions carried out at a normal blood flow in the measurement location enabling generation of first measured data indicative of a first time variation of the light response for each of said at least two parameter values, and at least two measurement sessions carried out at a condition of artificial kinetics in the measurement location enabling generation of second measured data indicative of a second time variation of the light response for each of said at least two parameter values; and (b) processing the first and second measured data to determine a first relation between the first time variations for the different parameter values and a second relation the second time variations for said different parameter values; and (c) utilizing the first and second relations to determine the at least one blood related parameter.

According to yet another broad aspect of the invention, there is provided a device for use in non-invasive measurements in a patient's body, the device comprising:

(a) a measurement unit comprising an electromagnetic field source assembly configured and operable for applying an external electromagnetic field to a measurement location on the body, and a detector arrangement configured and operable for detecting a response of the measurement location to the applied field and generating data indicative thereof;

(b) a pressure applying assembly configured and operable for applying over-systolic pressure to the body portion so as to create a condition of artificial kinetics in the measurement location characterized by a blood flow cessation;

(c) a control unit connectable to the measurement unit and to the pressure applying assembly for operating them so as to enable several measurement sessions on the measurement location, each measurement session carried out with the at least two different values of a controllable parameter, such that the measurement sessions include at least two measurement sessions carried out at a normal blood flow in the measurement location with substantially no application of pressure and at least two measurement sessions carried out at the condition of artificial kinetics in the measurement location; the control unit being configured for receiving and processing said data indicative of the response of the measurement location to the applied field to determine first measured data indicative of a first time variation of the response for each of said at least two parameter values while at the normal blood flow condition and second measured data indicative of a second time variation of the response for each of said at least two parameter values while at the artificial kinetics condition, thereby enabling determination of a first relation between the first time variations for the different parameter values and a second relation between the second time variations for said different parameter values, and utilizing said first and second relations to determine at least one blood related parameter.

According to yet another broad aspect of the invention, there is provided a device for use in non-invasive measurements in a patient's body, the device comprising:

(a) an optical measurement unit, which comprises a light source assembly, and a light detector arrangement configured and is operable to cause light responses of the illuminated location characterized by at least two different values of a controllable parameter; and generating data indicative thereof;

(b) a pressure applying assembly configured and operable for applying over-systolic pressure to the body portion so as to create a condition of artificial kinetics in the measurement location characterized by a blood flow cessation;

(c) a control unit connectable to the measurement unit and to the pressure applying assembly for operating them so as to enable several measurement sessions on the measurement location, each measurement session carried out with the at least two different values of the controllable parameter, such that the measurement sessions include at least two measurement sessions carried out at a normal blood flow in the measurement location with substantially no application of pressure and at least two measurement sessions carried out at the condition of artificial kinetics in the measurement location; the control unit being configured for receiving and processing said data indicative of the light response to determine first measured data indicative of a first time variation of the light response for each of said at least two parameter values while at the normal blood flow condition and second measured data indicative of a second time variation of the light response for each of said at least two parameter values while at the artificial kinetics condition, thereby enabling determination of a first relation between the first time variations for the different parameter values and a second relation between the second time variations for said different parameter values, and utilizing said first and second relations to determine at least one blood related parameter.

BRIEF DESCRIPTION OF THE DRAWINGS

In order to understand the invention and to see how it may be carried out in practice, preferred embodiments will now be described, by way of non-limiting example only, with reference to the accompanying drawings, in which:

FIGS. 3A-B and 4A-4C show experimental results for the technique of the invention, wherein

DETAILED DESCRIPTION OF EXEMPLARY EMBODIMENTS

Figure 1:
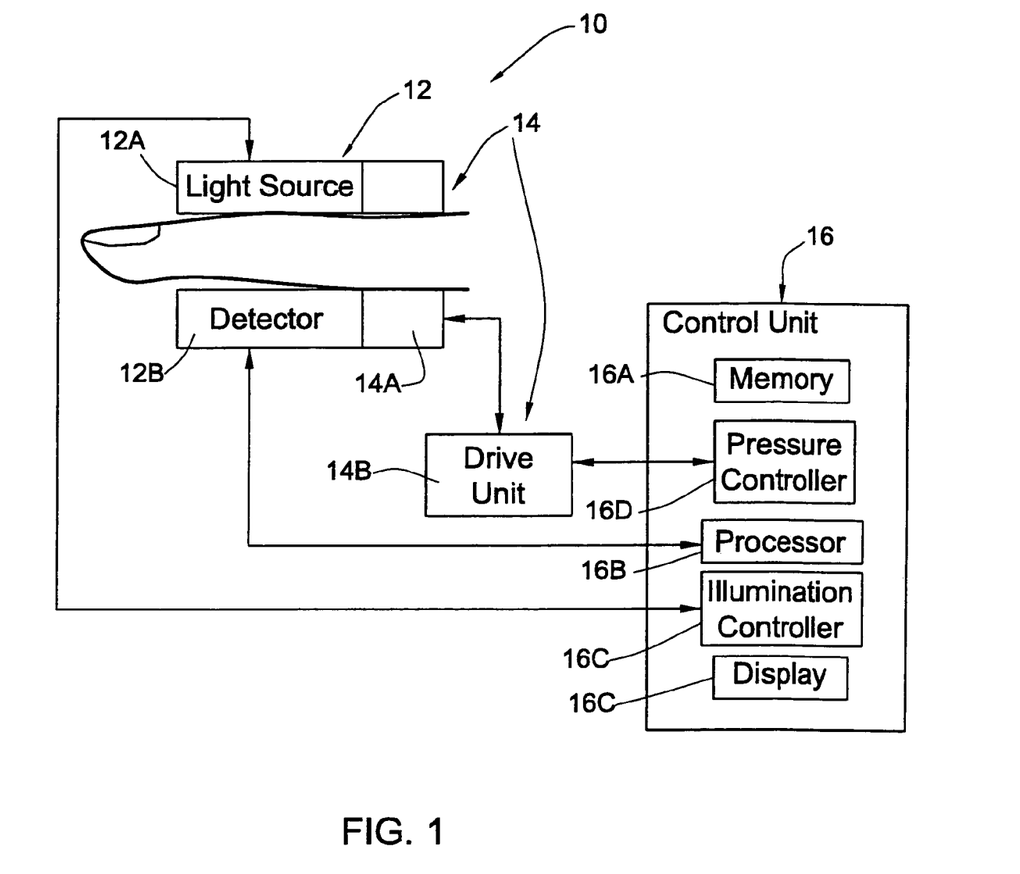
FIG. 1 is a block diagram of a device of the present invention, exemplified as being applied to a patient's finger.

Referring to FIG. 1, there is illustrated by way of a block diagram a device, generally designated 10, constructed and operated according to the invention. In the present example, the device is applied to a patient's finger (being configured as a clip-like or a ring-like device), but it should be understood that the invention is not limited to this specific example.

Device 10 includes a measurement unit 12, a pressure applying assembly 14, and a control unit 16. Measurement unit 12 and pressure applying assembly 14 may be made integral with each other (i.e., carried by a common housing, e.g., capable of being applied to the finger, e.g., a ring-like housing) or may be separate units (e.g., separate ring, or one being a ring and the other being a clip, as the case may be). Measurement unit 12 includes a source 12A of an external electromagnetic field to be applied to a measurement location in the body; and a detector 12B configured for detecting a response of the measurement location to the applied field. Field source 12A is operable (e.g., by control unit 16) to vary at least one of its operational parameters (e.g., a frequency of the applied field). Such a field may be light or electric signal. The response may be in the form of an optical, acoustic or electric signal.

In the present example, measurement unit 12 is an optical device configured to irradiate a region of interest (finger in the present example) with incident radiation of at least two different wavelengths in Visible, NIR or IR spectra, and detect a radiation response of the illuminated region. To this end, measurement unit 12 includes light source arrangement 12A (and possibly also a suitable light directing assembly, e.g., optical fiber(s) and/or a lens arrangement and/or polarizer arrangement); and light detector arrangement 12B (possibly equipped with suitable optics, and/or spectral filters, and/or polarizer arrangement). Light source arrangement 12A includes either a single broadband illuminator, or a plurality (at least two light source elements) emitting light of different wavelength ranges.

It should be understood that light source arrangement 12A may or may not be carried by the housing applied to the finger. For example, such a light source assembly may be a stand alone unit and an optical fiber arrangement is used for connecting the light source to the housing on the finger. Similarly, detector arrangement 12B may be mounted on the housing or may be connected thereto via an optical fiber arrangement. The housing (clip or ring) carrying the measuring unit is appropriately provided with optical windows allowing illuminating light to pass to the region of interest and allowing collection of the light response of the region of interest. In this connection, it should be understood that the device may be configured to operate with a reflection mode and/or transmission mode. Namely, the device may include one or more light detector (i.e., optical window(s) associated therewith) collecting light transmitted through the finger, and/or one or more light detector collecting light reflected (scattered) from the region of interest in the finger.

Pressure applying assembly 14 includes a cuff 14A configured for attaching to the patient's finger, and a drive unit 14B operated by control unit 16 for operating the squeezing of cuff 14A.

Control unit 16 is connectable to measurement unit 12 and pressure applying assembly 14 (via wires or wireless), and is configured to appropriately operate these units and to receive and process data indicative of the detected response of the measurement location. Control unit 16 is configured as a computer system including inter alia a memory utility 16A, a data processing utility 16B, and a data output utility (e.g., display) 16C. Also, control unit 16 includes a field source controller (an illumination controller) utility 16D and a pressure controller utility 16E associated with the drive unit 14B.

Figure 2A:
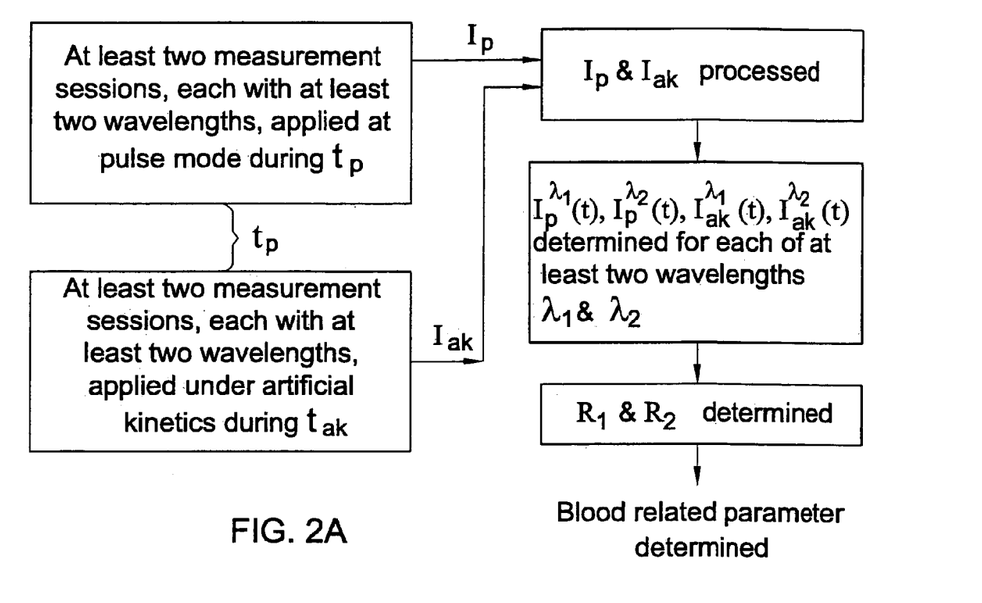
FIGS. 2A and 2B show two examples, respectively, of a method of the invention.
Figure 2B:
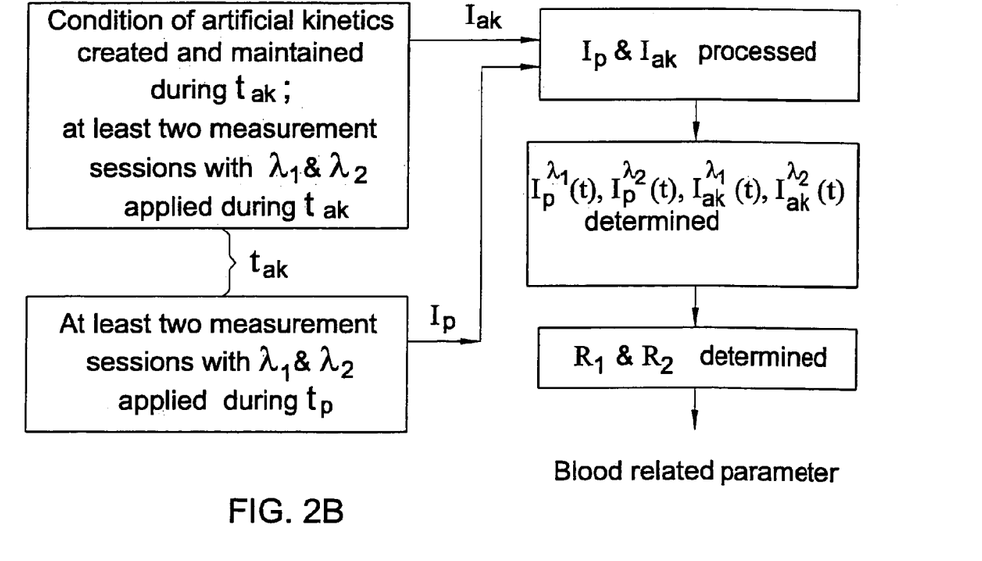

Reference is made to FIGS. 2A and 2B showing the operational steps in accordance with two examples, respectively, of a method of operating device 10 of the present invention. In the present example, pure optical measurements are considered, but it should be understood that the present invention is not limited to this specific example.

In the example of FIG. 2A, measurements are first taken at the steady state (pulse mode), and then under the artificial kinetics condition (occlusion mode). Accordingly, during a certain time period $t_p$, (e.g., about 20 seconds) pressure applying assembly 14 is kept inoperative, while measurement unit 12 is operated to apply two or more measurement sessions, each with at least two different wavelengths, and/or with at least two different states of polarization of the detected light (as described in the above-indicated U.S. Pat. No. 6,804,002 assigned to the assignee of the present application). Light source assembly 12A and detector arrangement 12B are operated to apply illumination (e.g., with at least two different wavelengths) to a measurement location (region of interest) and detect a light response, $I_p$, of the illuminated region (for at least two different values of the controllable parameter—that of wavelength of illumination in the present example). Data indicative of the light response, $I_p$, is received at the control unit.

After this time period $t_p$, a condition of artificial kinetics is created at the measurement location and maintained for a certain time period $t_{ak}$ such as not to cause irreversible changes in the fleshy medium (e.g., from a few seconds to about one minute), and optical measurements are applied to the measurement location during this time period $t_{ak}$. This is implemented by operating pressure applying assembly 14 to apply over-systolic pressure in the vicinity of the measurement location or upstream of the measurement location (with respect to a normal blood flow direction) so as to create blood flow cessation at the measurement location and maintain it during the cessation time $t_{ak}$, and operating the light source and detector assemblies to detect a light response, $I_{ak}$, of the measurement location for at least two measurement sessions while at the condition of artificial kinetics (under occlusion). Data indicative of the light response, $I_{ak}$, is received at the control unit. It should be noted that a certain short time (about 0.5 sec) exists from the moment when the pressure is initially applied and until the actual start of occlusion. Measurements taken during this time period may be disregarded, due to the unavoidable influence of motional and/or other artifacts causing non-monotonic fluctuations of the light response signal.

In the example of FIG. 2B, measurements are first taken at the occlusion mode (condition of artificial kinetics), and then during the steady state (pulse mode). Accordingly, pressure applying assembly 14 is operated to apply over-systolic pressure to the vicinity of the measurement location or upstream thereof and maintain this pressure during cessation time $t_{ak}$. Measurement unit 12 is operated to apply optical measurements (at least two measurement sessions, each with at least different wavelengths of light) during the cessation time. Similarly, measurement taken during a short time period from the moment when the pressure is initially applied and until the actual start of occlusion should be disregarded. Thereafter (after time $t_{ak}$), the pressure is released, and a transitional state of blood flow takes place, during about 2-3 seconds. Measurements taken during this time period may also be disregarded. After this transitional blood flow state, the normal blood flow is established, and light response, $I_p$, is measured in at least two measurement sessions.

Common for both examples, data indicative of the light responses $I_p$ and $I_{ak}$ are processed to determine measured data indicative of time variations of these light responses for each of the at least two wavelengths $\lambda_1$ and $\lambda_2$: $I^{\lambda 1}_p(t)$, $I^{\lambda 2}_p(t)$ and $I^{\lambda 1}_{ak}(t)$, $I^{\lambda 2}_{ak}(t)$. These measured data are further processed to determine a relation between the time variations of the light responses, namely a relation $R_1$ between functions $I^{\lambda 1}_p(t)$, $I^{\lambda 2}_p(t)$, and a relation $R_2$ between functions $I^{\lambda 1}_{ak}(t)$, $I^{\lambda 2}_{ak}(t)$. This allows for calculating the desired blood parameter. In this connection, it should be understood that the wavelength of illumination are appropriately selected for measuring a specific blood parameter.

The so-determined relations $R_1$ and $R_2$ between the time variations of the pulse mode and the occlusion mode light responses enables reduction of the time element both for the pulse related components and the occlusion related components of the optical response. The use of more than two wavelengths in each measurement session, allows for determining the relation between the light responses' variations for different pairs of wavelengths, which provide different sensitivities to different blood parameters.

Figure 3A:
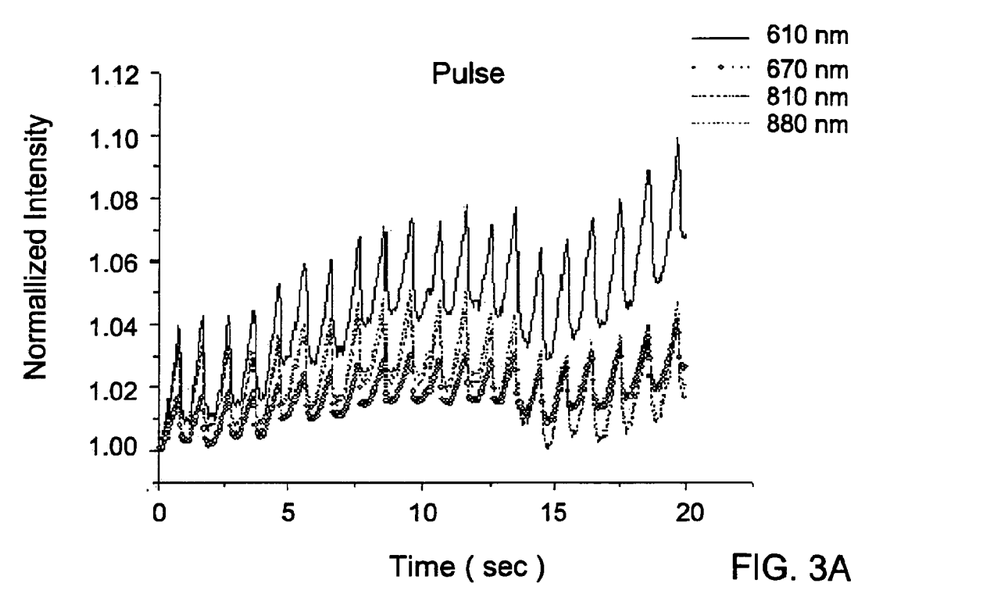
FIG. 3A shows the time variations of the pulse mode light responses for different wavelengths and FIG. 3B shows the time variations of the occlusion mode light responses for the same wavelengths, respectively.
Figure 3B:
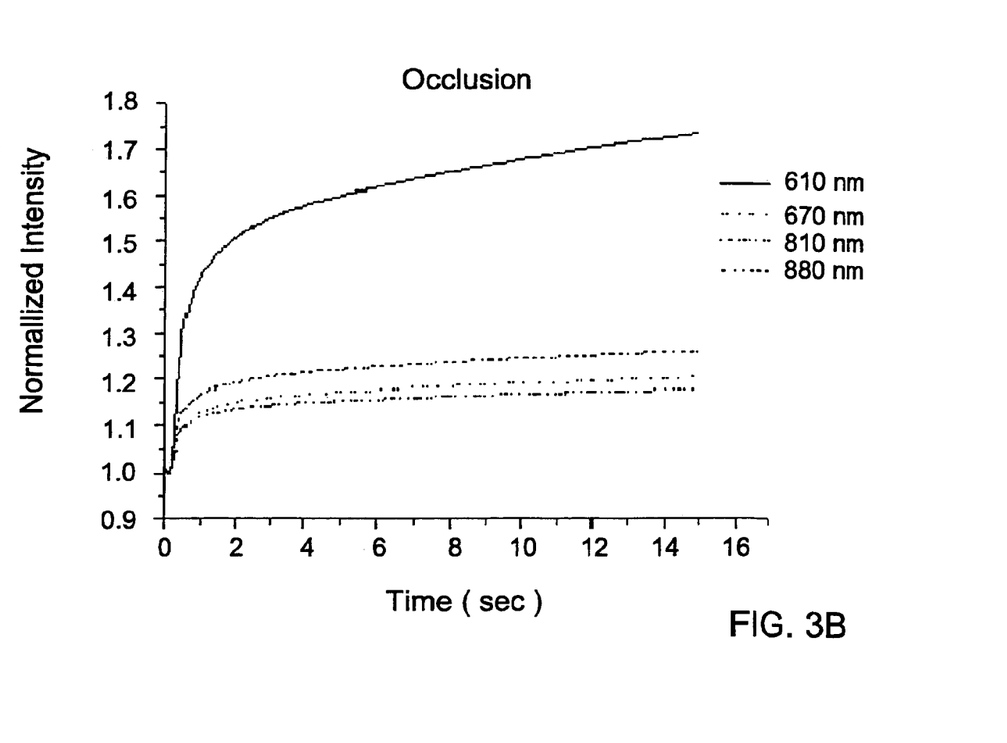

The following are experimental results of the invention. FIG. 3A shows the time variations of the pulse mode light responses, $I^1_p(t)$, $I^2_p(t)$, $I^3_p(t)$, $I^4_p(t)$, for, respectively, 610 nm, 670 nm, 812 and 880 nm wavelength; and FIG. 3B shows the time variations of the occlusion mode light responses, $I^1_{ak}(t)$, $I^2_{ak}(t)$, $I_{ak}(t)$, $I^4_{ak}(t)$, for the same wavelengths, respectively.

Figure 4A:
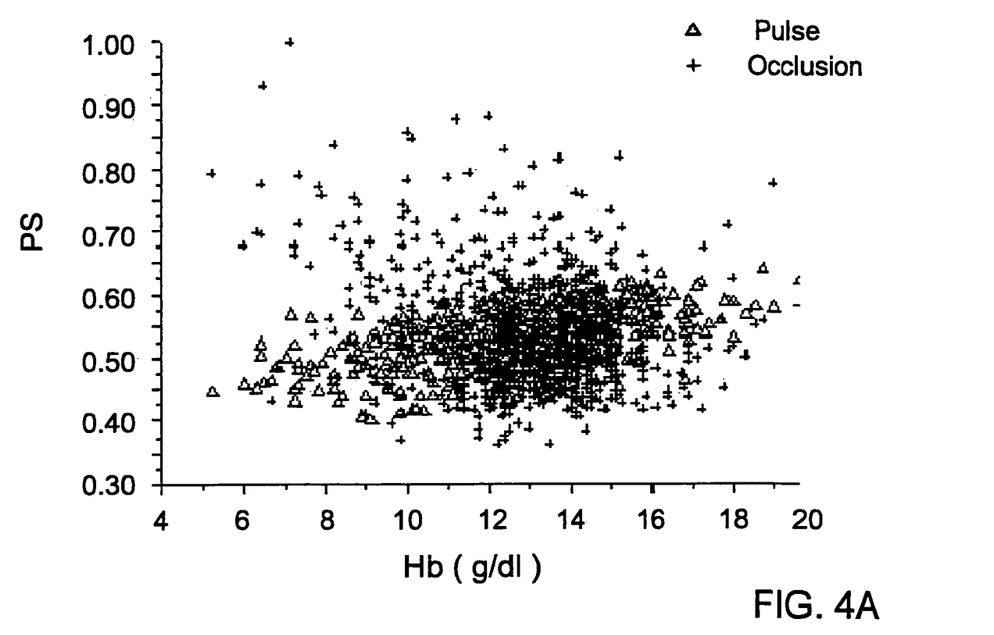
FIGS. 4A-4C show relations between the time variations of the light responses for the pulse and artificial kinetics modes (in terms of parametric slopes), for three different pairs of wavelengths, respectively.
Figure 4B:
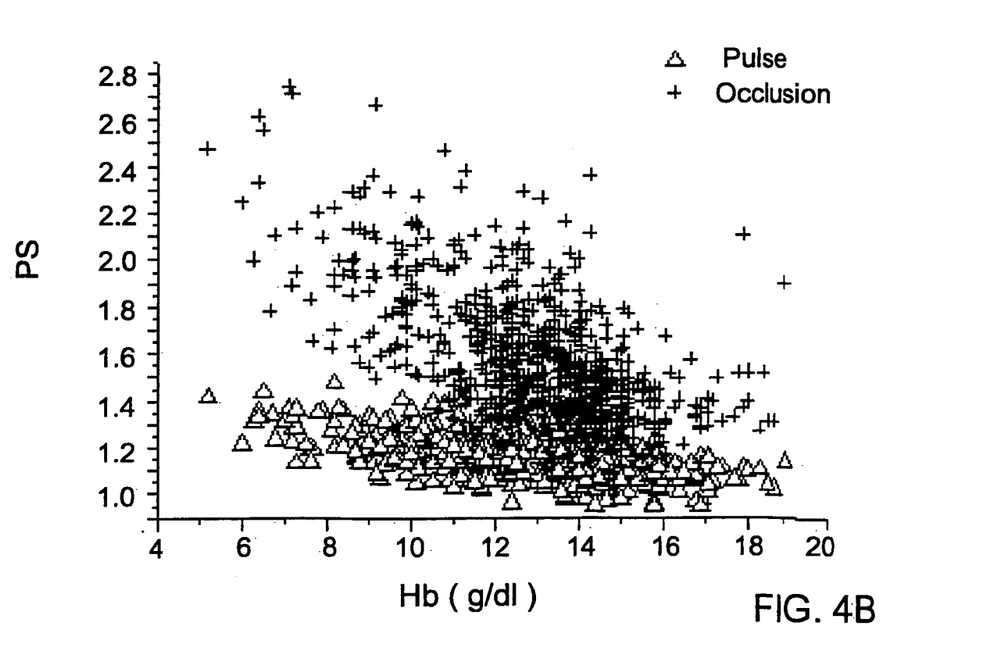
Figure 4C:
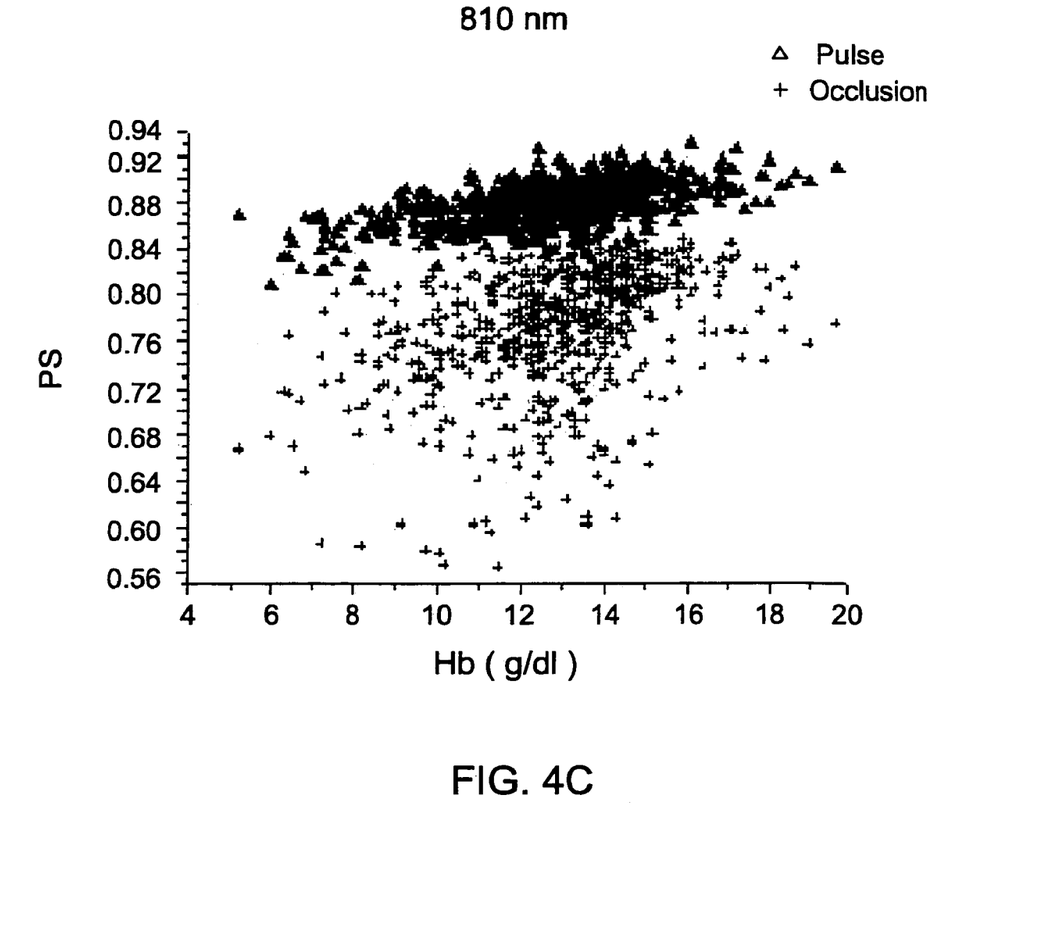

FIGS. 4A-4C show relations $R_1$-$R_2$, $R_1'$-$R_2'$ and $R_1''$-$R_2''$ for, respectively, the following pairs of wavelengths $\lambda_1$-$\lambda_2$: 670 nm-880 nm, 610 nm-880 nm, 810 nm-880 nm, where the wavelengths are selected for the concurrent determination of hemoglobin concentration and oxygen saturation, wavelength 880 nm being the so-called "reference wavelength". In the present example, the relation R is determined as a parametric slope (PS) namely a ratio between variation of the light response for one wavelength $\lambda_1$ and the variation of the light response for the reference wavelength $\lambda_1$, for example calculated as:

$$\frac{\partial \ln(I_{\lambda 1})/\partial t}{\partial \ln(I_{\lambda 2})/\partial t}.$$

As indicated above, different pairs of wavelengths provide different sensitivities to different blood parameters For example, the value of PS for 670 nm and 880 nm in the pulse mode (pulsatile signal) is most sensitive for HbO2/(Hb+HbO2) ratio (oxygen saturation), but reveals a small sensitivity to the hemoglobin concentration as well. The value of PS for 610 nm and 880 nm in the occlusion mode is very sensitive to hemoglobin/hematocrit, and is also sensitive at a certain degree to the blood Hb oxygen saturation. It should be noted that there are additional parameters, like blood flow and/or tissue hematocrit that can affect the PS value. Therefore, the use of additional pairs of wavelength is preferred in order to account or compensate for the variable parameters of management.

For the determination of Hb(SPO2) or glucose concentration, the following expression can be used:

$$Hb = \sum_{i=1}^{N} A_i \cdot (PS)_i \quad (1)$$

where $A_i$ are determined be using previous calibration; $(PS)_i$ are different pairs of parametric slopes; and i is a number of wavelength.

The calibration stage consists of the following: Measurement are taken in vivo for the population of patients, ranging from very low Hb values up to very high Hb values. Then, the reference Hb from the patients' blood is taken, using any standard Lab method. Thereafter, PS is calculated for the pulse and occlusion modes, and coefficients of the regression formula are determined using a standard mean least square calculation technique.

The examples of FIGS. 4A-4C demonstrate the differences between PS as a function of Hb for pulsatile and post occlusion signals.

Mathematically it means that volumetric PS is determined as:

$$PS(\text{pulse}) = \frac{\partial \text{Ln}(I_{\lambda 1})/\partial(x)}{\partial \text{Ln}(I_{\lambda ref})/\partial(x)} \quad (2)$$

wherein x is the blood volume pulsatile changes, and PS for post occlusion signal is determined as:

$$PS(\text{occlusion}) = \quad (3)$$

$$\frac{\partial \text{Ln}(I_{\lambda 1})/\partial(\mu_{\lambda transport1}(\lambda))}{\partial \text{Ln}(I_{\lambda ref})/\partial(\mu_{\lambda transport1}(\lambda ref))} \cdot \frac{\partial(\mu_{\lambda transport1}(\lambda))/\partial(t)}{\partial(\mu_{\lambda transport1}(\lambda ref))/\partial(t)}$$

wherein I is the optical response signal

The time dependent behavior of $\mu_{\lambda transport1}$ during the occlusion is the optical parameter driven by artificial kinetics.

Expressions (2) and (3) are supplemental to each other. The combination of these expressions provides additional information. The simplest combination is:

$$Hb = \sum_{i=1}^{N} A_i \cdot (PS(pusle))_i + \sum_{i=1}^{M} B_i \cdot (PS(\text{occlusion}))_i \quad (4)$$

For example, using only pulsatile component (expression 1) for Hb determination results in correlation of r=65%, using of only post occlusion signal on some dataset results in correlation r=63%. However, the combination of both signals (expression 4) provides a 85% correlation between the calculated and real value (invasively measured Hb value).

Naturally, if the explicit expressions (2) and (3) are provided in any form, then equations (2) and (3) can be solved symbolically or numerically as a set of equations.

It should be noted that this methodology can be used not only with the parametric slope being a primer parameter, but for any form or derivative of such a parametric slope or a differential thereof or Ln(I), or for any combination of them. The assessment of the following parameters that can be facilitated by using a combination of signals of pulse, artificial volumetric (pre-occlusion blood volume manipulation) and post-occlusion are: SPO2, Hb, Glucose, HbCO, MetHb.

Those skilled in the art will readily appreciate that many modifications and changes may be applied to the invention as hereinbefore exemplified without departing from its scope defined in and by the appended claims. In the method claims which follow, characters which are used to designate claim steps, are provided for convenience only and do not apply any particular order of performing the steps.

The invention claimed is:

1. A method for use in non-invasive measurements in a patient's body, the method comprising:
   (a) performing several measurement sessions on a measurement location on the body, each measurement session comprising illuminating a measurement location with light of at least two different wavelengths and detecting at least two light responses of the measurement location corresponding to said at least two different wavelengths of light, and generating data indicative of the detected response, wherein the measurement sessions include at least two measurement sessions carried out at a first condition of normal blood flow in the measurement location enabling generation of first measured data indicative of a first time variation of the response for each of said at least two different wavelengths, and at least two measurement sessions carried out at a second condition of artificial kinetics in the measurement location enabling generation of second measured data indicative of a second time variation of the response for each of said at least two different wavelengths; and
   (b) processing the first measured data to determine a first relation between the first time variations for the different wavelengths and processing the second measured data to determine a second relation between the second time variations for said different wavelengths, each of the first and second relations is determined as a parametric slope of the respective time functions of the responses; and
   (c) utilizing the first and second relations to determine a certain function between said first and second relations, thereby enabling determination of at least one blood related parameter BP as follows $$BP = \sum_{i=1}^{N} A_i \cdot (PS_1)_i + \sum_{i=1}^{M} B_i \cdot (PS_2)_i$$

wherein $A_i$ and $B_i$ are calibration coefficients; $(PS_1)_i$ and $(PS_2)_i$ are first and second parametric slopes obtained for the same pair of wavelengths; and i is a number of wavelengths.

2. The method of claim 1, wherein the condition of artificial kinetics is created by applying over-systolic pressure at the measurement location, or to a location on the body upstream of the measurement location with respect to a normal blood flow direction in the body.

3. The method of claim 1, wherein each of the measurement sessions includes more than two wavelengths of illumination.

4. The method of claim 1, wherein the light response includes light transmitted through and/or scattered from the body portion.

5. The method of claim 1, wherein a pair of the first and second parametric slopes $PS_1$ and $PS_2$ obtained for the same pair of wavelengths $\lambda_1$-$\lambda_2$ are determined as $$PS_1 = \frac{\partial \mathrm{Ln}(I^1 \lambda 1)/\partial(t)}{\partial \mathrm{Ln}(I^1 \lambda 2)/\partial(t)}$$

and $$PS_2 = \frac{\partial \mathrm{Ln}(I^2 \lambda 1)/\partial(t)}{\partial \mathrm{Ln}(I^2 \lambda 2)/\partial(t)}$$

wherein $I^1$ and $I^2$ are the first and second light responses.

6. The method of claim 1, wherein said at least two measurement sessions carried out at the normal blood flow condition are carried out either prior to said at least two measurement sessions under the artificial kinetics condition, or thereafter.

7. The method of claim 1, wherein said at least one blood related parameter includes one of a concentration of substance in blood and oxygen saturation.

8. The method of claim 7, wherein said substance includes at least one of the following: hemoglobin, hematocrit, glucose.

9. A device for use in non-invasive measurements in a patient's body, the device comprising:
   (a) a measurement unit comprising a light source assembly configured and operable for applying an external electromagnetic field to a measurement location on the body, and a light detector arrangement configured and operable for detecting a response of the measurement location to the applied field and generating data indicative thereof;
   (b) a pressure applying assembly configured and operable for applying over-systolic pressure to the body portion so as to create a condition of artificial kinetics in the measurement location characterized by a blood flow cessation;
   (c) a control unit connectable to the measurement unit and to the pressure applying assembly for operating them so as to enable several measurement sessions on the measurement location, each measurement session carried out with at least two different values of a controllable parameter, such that the measurement sessions include at least two measurement sessions carried out at a first condition of normal blood flow in the measurement location with no application of pressure and at least two measurement sessions carried out at the second condition of artificial kinetics in the measurement location; the control unit being configured for receiving and processing said data indicative of the response of the measurement location to the applied field to determine first measured data indicative of a first time variation of the response for each of said at least two parameter values while at the normal blood flow condition and second measured data indicative of a second time variation of the response for each of said at least two parameter values while at the artificial kinetics condition, thereby enabling determination of a first relation between the first time variations for the different parameter values and a second relation between the second time variations for said different parameter values, the control unit being programmed to determine each of the first and second relations as a parametric slope of the respective time functions of the responses and utilizing said first and second relations to determine at least one blood related parameter BP as follows $$BP = \sum_{i=1}^{N} A_i \cdot (PS_1)_i + \sum_{i=1}^{M} B_i \cdot (PS_2)_i$$

wherein $A_i$ and $B_i$ are calibrated coefficients; $(PS_1)_i$ and $(PS_2)_1$ are first and second parametric slopes obtained for the same pair of wavelengths; and i is a number of wavelengths.

10. The device of claim 9, wherein the control unit operates the measurement unit and the pressure applying assembly such that said at least two measurement sessions carried out at the normal blood flow condition are performed either prior to said at least two measurement sessions under the artificial kinetics condition, or thereafter.

11. The device of claim 9, wherein the control unit is preprogrammed to determine a pair of the first and second parametric slopes $PS_1$ and $PS_2$ for the same pair of wavelengths $\lambda_1$-$\lambda_2$ as:

$$PS_1 = \frac{\partial \mathrm{Ln}(I^1 \lambda 1)/\partial(t)}{\partial \mathrm{Ln}(I^1 \lambda 2)/\partial(t)}$$

and $$PS_2 = \frac{\partial \mathrm{Ln}(I^2 \lambda 1)/\partial(t)}{\partial \mathrm{Ln}(I^2 \lambda 2)/\partial(t)}$$

wherein $I^1$ and $I^2$ are the first and second light responses.

* * * * *